United States Patent [19]

Linder

[11] Patent Number: 5,190,036

[45] Date of Patent: Mar. 2, 1993

[54] ABDOMINAL BINDER FOR EFFECTUATING COUGH STIMULATION

[76] Inventor: Steven H. Linder, 5093 Woodbrae Ct., Saratoga, Calif. 95070

[21] Appl. No.: 662,027

[22] Filed: Feb. 28, 1991

[51] Int. Cl.⁵ ............................................. A61N 1/22
[52] U.S. Cl. .................................... 128/421; 128/798; 128/419 G
[58] Field of Search ............... 128/419 G, 421, 423 R, 128/798, 802, 379, 384

[56] References Cited

U.S. PATENT DOCUMENTS

| | | | |
|---|---|---|---|
| 2,428,980 | 10/1947 | McCann | 128/721 |
| 2,711,729 | 6/1955 | Hofmann | 128/419 G |
| 3,077,884 | 2/1963 | Batrow et al. | 128/423 R |
| 4,305,402 | 12/1981 | Kitmas | 128/421 |
| 4,381,012 | 4/1983 | Russek | 128/802 |
| 4,558,704 | 12/1985 | Petrofsky | 128/423 R |
| 4,729,377 | 3/1988 | Granek et al. | 128/419 G |
| 4,763,660 | 8/1988 | Kroll et al. | 128/640 |
| 4,827,935 | 5/1989 | Geddes et al. | 128/639 |
| 5,062,414 | 11/1991 | Grim | 128/362 X |
| 5,067,495 | 11/1991 | Brehm | 128/421 |
| 5,081,989 | 1/1992 | Graupe et al. | 128/421 X |

OTHER PUBLICATIONS

Reines et al., "Pulmonary Complications of Acute Spinal Cord Injuries", vol. 21, No. 2, 1987.
Geddes, et al., "Electrically Produced Artificial Ventilation", vol. 22, No. 5, 1988 the OEM Cof-Flator Portable Cough Machine.

Primary Examiner—Lee S. Cohen
Assistant Examiner—Samuel Gilbert
Attorney, Agent, or Firm—Nathan N. Kallman

[57] ABSTRACT

An apparatus for stimulating coughing in quadriplegic patients comprises an electrode belt that is attached in close contact and located in a given area of the abdomen of a patient. Pulse trains of specified duration and frequency having specified amplitudes and pulse widths are applied to the belt electrodes to provide momentary spasm-inducing stimulation to effectuate coughing and to clear the respiratory channels of the patient.

13 Claims, 2 Drawing Sheets 5,190,036

ABDOMINAL BINDER FOR EFFECTUATING COUGH STIMULATION

FIELD OF THE INVENTION

This invention relates to a method and means for stimulating coughing and in particular for electrical stimulation of coughing in quadriplegia patients.

BACKGROUND OF THE INVENTION

Description of the Prior Art

Quadriplegics, by definition, have impairment of all four limbs, depending on the level and the extent of the spinal cord injury. Even though there may be some residual upper limb or hand function, the chest and abdominal wall muscles below the shoulders are generally paralyzed.

Respiratory impairment is caused by loss of supraspinal control of respiratory muscles below the lesion. Normally ventilation is a complex interaction between the muscles of the chest, abdominal wall, and diaphragm. Spinal cord injury leads to paralysis of inspiratory and expiratory muscles. Loss of abdominal and chest wall expiratory muscles reduce ability to cough and clear secretions.

In the 1950's mortality from respiratory failure in quadriplegia was 100%, decreasing to 11% in the early 1980's. Respiratory problems now comprise a major cause of death in the acute and chronic phases of spinal cord injury (SCI).

A sensitive indicator of respiratory impairment due to neuromuscular disorders is the maximum expiratory pressure (MEP). MEP is greatly decreased due to paralysis of the intercostal and abdominal muscles. Expiration is mostly a passive action, dependent on the recoil of the inflated chest. The impairment of active expiratory pressures results in impaired cough.

The normal MEP ranges from 150–200 cm $H_2O$. SCI patients have an MEP reduced to 30% or less. One study showed intrathoracic pressures in SCI patients, as measured by esophageal balloon manometry, to be far below those of normal subjects during coughing.

In pulmonary management of quadripleqia, secretion control is vital to prevent ateleotasis and pneumonia. Fiber optic bronchoscopy and endotracheal suction may be used to prevent such problems. An oscillating kinetic treatment table, such as a Rotorest (trademark of Kinetic Concepts) bed, facilitates postural drainage. However, suction and the use of an artificial airway such as a tracheostomy have the potential for damage to the bronchi due to irritation and trauma that can lead to infection. Suction may also dangerously lower the alveolar oxygen pressure. Chest physiotherapy with chest percussion by a trained attendant is required for patients lacking the ability to cough.

One prior approach to stimulate coughing is known as quad coughing, or huffing, which is the practice by an attendant of pushing the abdomen forcefully to generate the positive airway pressure needed to expel mucus. It has been shown that good quad (quadriplegic) cough results are obtained with full chest insufflation and with the patient in a supine position. Coughing attempts can also be improved by bending the patient forward when sitting.

A prior art device known as the "Cof-Flator" (trademark of Shampaine Industries) was used in polio patients to clear respiratory secretions by delivering a positive pressure air volume followed by a negative pressure. This method required an attendant trained in the use of the "Cof-Flator" device. However the use of this device has the potential for damage to the airways due to excessive suction.

It has also been observed that the loss of nerve supply of the gut and bladder reduces the ability to control voiding of the bowel and bladder and therefore requires an attendant to compress the abdomen of a patient manually. By stimulating the paralyzed abdominal wall to contract, an improved ability to control voiding of the bowel and bladder may be attained for quadriplegic patients.

SUMMARY OF THE INVENTION

An object of this invention is to provide a method and means for producing a brief, maximal activation of the abdominal muscles in order to deliver a forceful, impulsive expiration and coughing.

Another object of this invention is to provide a method and means for activating coughing in a patient that is not harmful to the abdominal and thoracic organs.

Another object is to provide electrical stimulation of partially or totally paralyzed muscles in quadriplegic patients.

A further object is to provide means for a quadriplegic patient to stimulate coughing without the aid of an attendant.

An additional object is to provide means for increasing intra-abdominal pressures in quadriplegic patients to improve the ability of controlling voiding of the bowel and bladder.

BRIEF DESCRIPTION OF THE DRAWINGS

The invention will be described with reference to the drawing in which.

DETAILED DESCRIPTION OF THE PREFERRED EMBODIMENT

Figure 1:
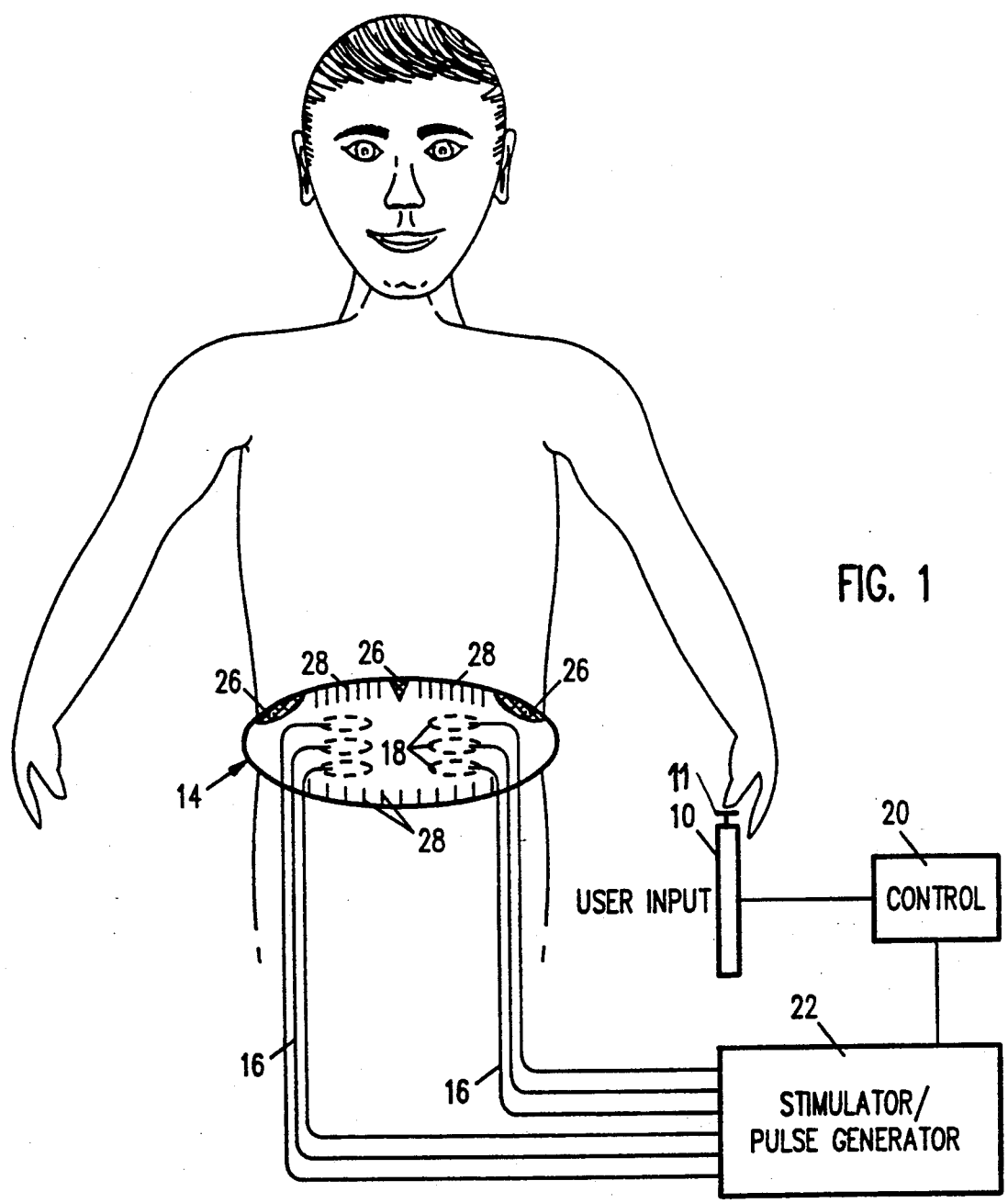
FIG. 1 is a representation of a patient wearing the electrical cough binder of this invention, and showing in block form the electrical circuitry associated with the binder.
Figure 5:
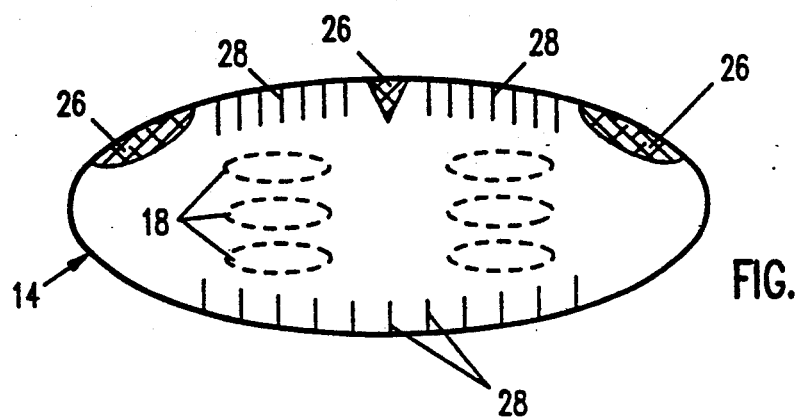
FIG. 5 is a representation of the electrode belt.

With reference to FIG. 1, an elastic abdominal binder or electrode belt 14 is securely positioned on the abdomen of a patient who may be suffering from respiratory problems, such as experienced by quadriplegic patients. The belt is made of a durable material, such as cotton elastic cloth, by way of example. Fasteners (not shown), made from Velcro for example, are attached to the belt 14 to aid in snapping the belt around the abdomen of the patient and to maintain the belt in close contact adjacent to the abdomen of the patient. The belt is made to be about 10–12 inches in width with a circumference of about 40 inches to accommodate the waistline of the wearer. The belt 14 has flexible stays, preferably of metal such as spring steel, to prevent bunching of the belt material. The binder 14 can be made in various sizes to accommodate the physical characteristics of different patients.

A first set of anatomical markers or indicators 26 are incorporated on the belt to aid in optimum placement for enhanced stimulation. The markers 26, shown as a centrally located inverted triangle and two spaced semi-elliptical regions, are located at the area beneath the xiphoid process and costal margins. A second set of markers 28 comprising spaced lines or dots, substantially equally spaced, across the top and bottom edges of the belt 14, are used to indicate abdominal girth changes that occur between maximum inspiration and expiration to establish the timing of cough stimulation.

An electrode assembly 18 comprising pairs of electrodes is attached to the belt 14 which holds the electrodes in place on the abdomen of the patient. The electrodes are preferably made of carbonized conductive silicone rubber and are attached by means of Velcro backing, for example, to the inner surface of the front portion of the belt 14. When strapped to the patient, the electrodes make close contact with the skin of the patient. When in use, the electrodes 18 may have a conductive gel applied to the surfaces that make contact with the skin of the patient's abdomen. The electrodes 18 are spaced and located at specified positions to ensure optimum application of electrical pulses and maximum stimulation at the abdominal wall motor point. The cough binder used in the preferred embodiment had four pairs or a total of eight electrodes.

The electrodes 18 are connected to a pulse generator/stimulator module 22 that generates pulse signals of a predetermined amplitude and duration and provides stimulus pulses to the electrode assembly. The pulse generator 22 generates one or more trains of pulse signals in response to the activation of a user-input module 10 which includes a momentary spring-operated push button 11 that can be actuated by the user of the belt 14.

In accordance with this invention, the pulse generator 22 produces pulse trains with pulse widths between 50 to 500 microseconds, which is determined by the timing network of a control circuit 20 coupled between the user-input module 10 and the pulse generator 22. The repetition rate of the pulse signal is between 40–70 Herz (Hz), preferably 50 Hz. In a specific implementation of the invention, the pulse train comprises a single burst of pulses of about two seconds duration. The pulse width was set at 300 microseconds with a frequency of 50 Hz, and with an intensity of 100% of maximum with virtual zero rise time and having a biphasic waveform. Alternatively, each pulse train may be a series of four bursts of pulses, each burst being about 0.25 second long with a separation of 0.25 second between adjacent bursts.

The pulse generator/stimulator comprises one or more stimulator circuits, each of which converts one of the pulse trains generated by the pulse generator into a train of stimulus pulses. The stimulator circuits serve as current sources wherein the stimulus pulses are constant current pulses having amplitudes in the range of about 50–200 milliamperes. Each stimulator circuit has the capability of supplying a maximum voltage of 100–200 volts. In an alternative implementation, the stimulator circuits are voltage sources wherein the stimulus pulses are constant voltage pulses having amplitudes in the range of 50–200 volts. The pulses typically have rectangular, symmetrical biphasic or asymmetrical biphasic waveforms. The pulse signals are passed from the stimulator to the electrodes 18 via connecting leads 16. Each stimulator circuit is connected to one of the pairs of electrodes 18. It is desirable to have at least two stimulator channels, one for the right abdominal area and one for the left abdominal area.

In operation, when a patient experiences a respiratory problem and difficulty in producing coughing to clear the lungs, the patient depresses the spring-operated button 11 which is part of the user-input module 10. The depressed button 10 enables the control circuit 20 that controls the width and amplitude of the pulse signal generated by the pulse generator 22. The power source to the system may be from a 110 volt commercial supply available from a conventional wall socket. In such case a transformer and voltage regulator are provided between the apparatus and the power source to ensure that a proper voltage is fed to the circuitry associated with the electrode belt. For portability, a wheel chair battery or a self-contained portable battery unit can be used as a power source. An indicator light (not shown) can indicate when the battery power source has a low charge and needs recharging or replacement.

The patient needs to be trained to use the electrode belt apparatus by inhaling deeply, then simultaneously exhaling and activating the switch button to maximize the coughing function, and then repeating the steps as needed.

Figure 2:
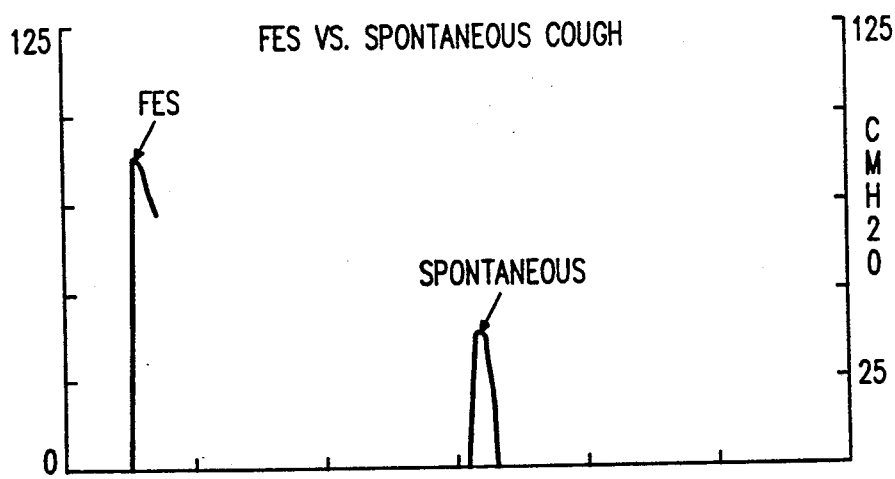
FIG. 2 is a plot of functional electrical stimulation (FES) against spontaneous unassisted cough depicting an MEP tracing for an individual quadriplegic showing increased MEP with abdominal FES, in accordance with the invention.
Figure 3:
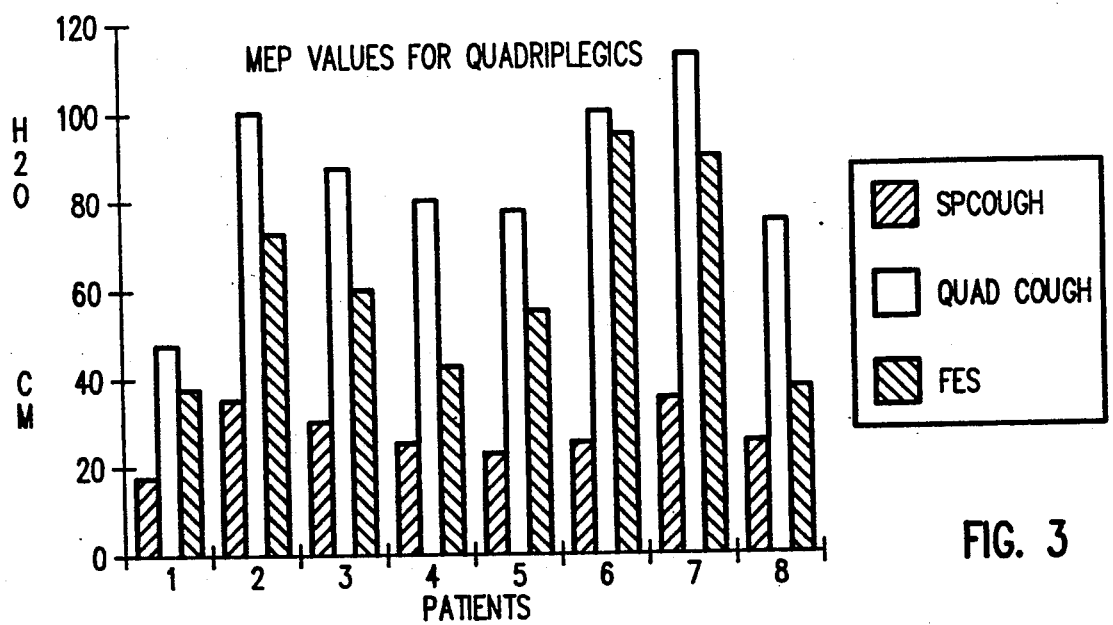
FIG. 3 is a bar diagram showing maximum expiratory pressure (MEP) values for quadriplegics and MEP increase over the spontaneous cough MEP with either quad cough delivered by a trained attendant or abdominal FES measuring $H_2O$ cm. for a number of patients.
Figure 4:
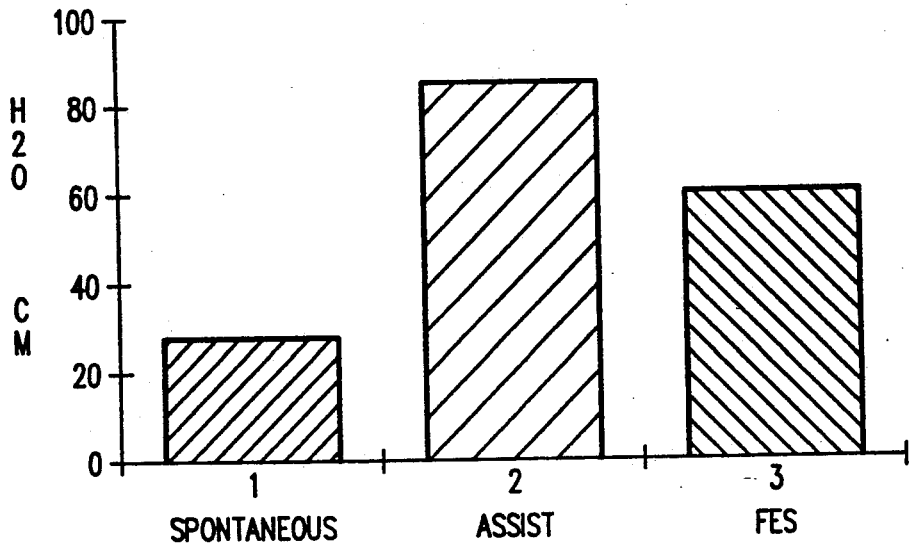
FIG. 4 is a plot of $H_2O$ cm. against spontaneous cough, assisted cough and FES cough showing average MEP values and the MEP increase over spontaneous cough MEP with either quad cough delivery by a trained attendant or abdominal FES.

The novel technique employing the apparatus disclosed herein has proven significantly effective in treating quadriplegic patients and in effect saving lives when respiratory failure due to airway occlusion by mucus occurs. FIGS. 2–4 show the effective MEP increase obtained for individual quadriplegics using the abdominal FES method of this invention, as compared to a spontaneous cough MEP, as measured during tests of the novel apparatus.

By virtue of the electrical cough binder of this invention, a quadriplegic can self-induce coughing for clearing the respiratory passages without the help of an attendant. The electrode belt is also useful with persons experiencing choking due to a foreign body in the trachea. The momentary spasm-inducing action resulting from the applied series of pulses of predetermined amplitude and duration increases intrathoracic pressures thus resulting in enhancing and improving coughing in quadriplegic patients. In addition the abdominal binder disclosed herein may be used for stimulating a paralyzed abdominal wall to control the voiding of the bowel and bladder of a quadriplegic patient.

What is claimed is:

1. An apparatus for inducing coughing by electrical stimulation resulting from increasing intrathoracic pressures in a human with a physical disability comprising:
an electrode belt having at least one electrode for attachment to the abdominal area of a person;
means coupled to said at least one electrode for providing at least one pulse train of a predetermined duration with pulses having a given amplitude for stimulating the abdominal muscles of the person, wherein said pulse train providing means includes a pulse generator for generating said pulse train and a stimulator circuit means for converting said pulses to stimulus pulses of a specified amplitude and duration; and control means coupled to said pulse generator and stimulator circuit means for controlling the amplitude and width of said pulses.

2. An apparatus as in claim 1, wherein said electrode belt comprises at least six electrodes mounted to said belt and positioned at spaced locations relative to the abdominal muscles of a person when said belt is attached to the person; and markers on said belt for delineating the placement of said belt on the person so that said electrodes are positioned beneath the xiphoid process and costal margins of the person.

3. An apparatus as in claim 2, wherein said electrodes are made of conductive carbonized silicone rubber.

4. An apparatus as in claim 3, including a gel material coated on the surfaces of said electrodes.

5. An apparatus as in claim 1, wherein said electrode belt comprises an elastic band; fastening means joined to said band to enable attachment of said belt in close contact with the abdomen of a person; and flexible stays formed with said belt to maintain the belt in a substantially rigid shape.

6. An apparatus as in claim 1, comprising a user-input module including a push button switch means for connecting a power source to energize said apparatus to generate pulses for delivery to the abdominal area of the person.

7. An apparatus as in claim 6, wherein said pulses are constant current pulses having amplitudes in the range of about 50-200 milliamperes.

8. An apparatus as in claim 1, wherein said pulses are characterized by widths between 50-500 microseconds, a repetition rate between 40-70 Hertz, and an amplitude between 50-200 volts.

9. An apparatus as in claim 8, wherein the pulse width is 300 microseconds, the frequency of said pulses is 50 Hertz, and said pulses have a biphasic waveform.

10. An apparatus as in claim 1, wherein said pulse train comprises a series of four bursts of pulses, each burst being about 0.25 second in duration with a separation of 0.25 second between adjacent bursts.

11. An apparatus as in claim 1, wherein said electrode belt includes a first set of markers for aligning said belt with the anatomy of said human; and a second set of markers for indicating changes in the abdominal girth of said human.

12. An apparatus as in claim 11, wherein said second set of markers comprise a series of equally spaced lines or dots disposed across said electrode belt.

13. A method for stimulating coughing comprising the steps of:

attaching an electrode belt having at least one electrode to the abdomen of the patient so that said at least one electrode of the belt is located in close contact with the abdominal area beneath the xiphoid process and costal margins of the patient; and depressing a momentary push button switch to activate a pulse generator and stimulus pulse circuit and directing stimulus pulses from said stimulus pulse circuit to said at least one electrode of the belt while the patient is exhaling so that an electrical stimulus is delivered to the abdominal area of the patient thereby increasing the intrathoracic pressures to produce coughing by the patient.

* * * * *